US011869181B2

(12) United States Patent
Nakamura et al.

(10) Patent No.: US 11,869,181 B2
(45) Date of Patent: Jan. 9, 2024

(54) DETERMINATION METHOD

(71) Applicant: FUJIFILM Corporation, Tokyo (JP)

(72) Inventors: Sohichiro Nakamura, Ashigarakami-gun (JP); Sho Onozawa, Ashigarakami-gun (JP); Ryusuke Osaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 492 days.

(21) Appl. No.: 17/182,569

(22) Filed: Feb. 23, 2021

(65) Prior Publication Data

US 2021/0174507 A1 Jun. 10, 2021

Related U.S. Application Data

(63) Continuation of application No. PCT/JP2019/031862, filed on Aug. 13, 2019.

(30) Foreign Application Priority Data

Sep. 28, 2018 (JP) ................. 2018-185583

(51) Int. Cl.
*G06T 7/00* (2017.01)
*G06T 7/62* (2017.01)
(Continued)

(52) U.S. Cl.
CPC ............ *G06T 7/0012* (2013.01); *C12Q 1/02* (2013.01); *G01N 21/453* (2013.01); *G06F 17/18* (2013.01);
(Continued)

(58) Field of Classification Search
CPC .................. G06T 7/0012; G06T 7/62; G06T 2207/10056; G06T 2207/10064;
(Continued)

(56) References Cited

U.S. PATENT DOCUMENTS

2010/0060897 A1* 3/2010 Gustafsson ............ G02B 21/14
356/458
2012/0315620 A1 12/2012 Watakabe et al.
(Continued)

FOREIGN PATENT DOCUMENTS

JP 2006-522805 A 10/2006
JP 2009-521216 A 6/2009
(Continued)

OTHER PUBLICATIONS

Japanese Office Action for corresponding Japanese Application No. 2020-548139, dated Feb. 1, 2022, with English translation.
(Continued)

*Primary Examiner* — Dhaval V Patel
(74) *Attorney, Agent, or Firm* — Birch, Stewart, Kolasch & Birch, LLP

(57) ABSTRACT

A determination method of non-destructively and easily determining a state of an aggregate of a plurality of cells formed by three-dimensional culture is provided. A determination method according to the disclosed technology includes generating a phase difference image of an aggregate of a plurality of cells from a hologram obtained by imaging the aggregate, deriving a first index value that indicates a randomness of an array of a phase difference amount in a plurality of pixels constituting the phase difference image, and determining a state of the cells constituting the aggregate on the basis of the first index value.

20 Claims, 16 Drawing Sheets

(51) Int. Cl.
    *C12Q 1/02*    (2006.01)
    *G01N 21/45*   (2006.01)
    *G06F 17/18*   (2006.01)

(52) U.S. Cl.
    CPC ...... *G06T 7/62* (2017.01); *G06T 2207/10056* (2013.01); *G06T 2207/10064* (2013.01); *G06T 2207/30024* (2013.01)

(58) Field of Classification Search
    CPC . G06T 2207/30024; G06T 2207/20056; G06T 2207/20076; C12Q 1/02; G01N 21/453; G01N 33/5032; G01N 33/5073; G06F 17/18; G06V 20/695; G03H 1/0866; G03H 2001/0883; C12M 1/34
    See application file for complete search history.

(56)  References Cited

U.S. PATENT DOCUMENTS

| | | | |
|---|---|---|---|
| 2014/0073002 A1 | 3/2014 | Yamauchi et al. | |
| 2014/0375792 A1 | 12/2014 | Yaqoob et al. | |
| 2017/0261930 A1 | 9/2017 | Mathuis et al. | |
| 2017/0358081 A1* | 12/2017 | Tsumura | G01N 21/253 |
| 2019/0250558 A1* | 8/2019 | Javidi | G01N 21/453 |
| 2020/0310349 A1* | 10/2020 | Kim | G03H 1/0866 |
| 2020/0342599 A1 | 10/2020 | Nakamura et al. | |

FOREIGN PATENT DOCUMENTS

| | | |
|---|---|---|
| JP | 2013-236564 A | 11/2013 |
| JP | 2015-192644 A | 11/2015 |
| JP | 2016-28607 A | 3/2016 |
| WO | WO2004/079007 A2 | 9/2004 |
| WO | WO2007/122655 A2 | 11/2007 |
| WO | WO2014/041935 A1 | 3/2014 |
| WO | WO 2019/176427 A1 | 9/2019 |

OTHER PUBLICATIONS

Awatsuji, "Development of three-dimensional motion image measuring method for cells by parallel phase-shifting digital holographic microscopy and device therefor," Reciclout, No. 35, Dec. 2009, pp. 10-15 (8 pages total), with Engiish translation.

International Preliminary Report on Patentability and Written Opinion of the International Searching Authority (Forms PCT/IB/326, PCT/IB/373 and PCT/ISA/237) for corresponding International Application No. PCT/JP2019/031862, dated Apr. 8, 2021, with English translation.

International Search Report (From PCT/ISA/210) for corresponding International Application No. PCT/JP2019/031862, dated Nov. 19, 2019, with English translation.

Extended European Search Report for corresponding European Application No. 19865460.0, dated Oct. 21, 2021.

Singh et al., "Lateral shearing digital holographic imaging of small biological specimens," Optics Express, vol. 20, No. 21, Oct. 8, 2012, pp. 23617-23622.

* cited by examiner

UNDIFFERENTIATED RATE 99%

$\lambda = 13.6$

UNDIFFERENTIATED RATE 99%

$\lambda = 13.6$

UNDIFFERENTIATED RATE 87%

$\lambda = 18.9$

UNDIFFERENTIATED RATE 87%

$\lambda = 18.9$

SURVIVAL RATE 87.3%

$\lambda = 5.77$

SURVIVAL RATE 87.3%

$\lambda = 5.77$

SURVIVAL RATE 59.2%

$\lambda = 11.08$

SURVIVAL RATE 59.2%

$\lambda = 11.08$

DETERMINATION METHOD

CROSS-REFERENCE TO RELATED APPLICATIONS

This application is a Continuation of PCT International Application No. PCT/JP2019/031862 filed on Aug. 13, 2019, which claims priority under 35 U.S.C. § 119(a) to Japanese Patent Application No. 2018-185583 filed on Sep. 28, 2018. Each of the above application(s) is hereby expressly incorporated by reference, in its entirety, into the present application.

BACKGROUND OF THE INVENTION

1. Field of the Invention

The disclosed technology relates to a determination method for determining a state of an aggregate of a plurality of cells.

2. Description of the Related Art

As a technology for evaluating or determining a state of a cell, for example, the following technology is known. WO2014/041935A discloses a method for discriminating a degree of differentiation of a pluripotent stem cell using a flatness of a surface of one cell or a flatness of a surface of a cell population as an index of a degree of differentiation.

JP2016-028607A discloses a method for discriminating between a differentiated colony containing differentiated pluripotent stem cells and an undifferentiated colony containing only undifferentiated pluripotent stem cells and a multilayered colony containing multilayered pluripotent stem cells on the basis of brightness in a captured image. In this method, a colony having a brightness region brighter than the first threshold value of brightness is determined to be a differentiated colony. In addition, a colony having a brightness region equal to or darker than the first threshold value is determined to be an undifferentiated colony. In addition, a colony having a brightness region equal to or darker than the first threshold value and equal to or brighter than the second threshold value is determined as an undifferentiated colony. Further, a colony having a brightness region darker than the second threshold value is determined to be a multilayered colony.

JP2013-236564A discloses a cell evaluation method characterized by comprising an image input step of inputting a captured image obtained by imaging a cell in a neural differentiation process, a neurite extraction step of extracting a neurite appearing in the cell in the neural differentiation process from an original image based on the captured image, and a neurite correspondence determination step of determining a state of the extracted neurite.

JP2006-522605A discloses a method for presenting a cellular state, the method including a step of obtaining a temporal profile of a cell by monitoring over time a genetic state related to at least one gene selected from gene derived from the cell, and a step of presenting the temporal profile.

SUMMARY OF THE INVENTION

As a culture method capable of mass production of cells, a three-dimensional culture method is known in which a sphere that is an aggregate of cells are cultured in a suspended state in a medium. In the production process of cells by the three-dimensional culture, a technology for non-destructively and simply evaluating the quality of cells in the state of spheres is required from the viewpoint of easy process control. However, at the present time, a method for evaluating spheres having various sizes randomly present in a three-dimensional space has not been established, and in particular, it is difficult to directly observe a density and survival situation of cells inside the sphere. For this reason, as disclosed in WO2014/041935A, JP2016-028607A, and JP2013-236564A, evaluation is performed by applying a conventional two-dimensional culture method, but as the number of cells to be cultured increases, the number of evaluation steps increases, and thus much manpower and much time are required. In the evaluation to which the conventional two-dimensional culture method is applied, a treatment involving cell destruction such as decomposing the sphere into a single cell or adding a fluorescent coloring agent as disclosed in JP2006-522605A is required.

An object of the disclosed technology is to non-destructively and easily determine a state of an aggregate of a plurality of cells formed by three-dimensional culture.

A determination method according to the disclosed technology includes generating a phase difference image of an aggregate of a plurality of cells from a hologram obtained by imaging the aggregate, deriving a first index value that indicates a randomness of an array of a phase difference amount in a plurality of pixels constituting the phase difference image, and determining a state of the cells constituting the aggregate on the basis of the first index value. According to the determination method of a disclosed technology, the state of the aggregate of a plurality of cells formed by three-dimensional culture can be determined non-destructively and easily.

The first index value may be a value determined according to a degree of deviation from a circle of a shape of a region surrounded by an equiphase line connecting pixels of the same phase difference amount in the phase difference image. Specifically, in a case where a minimum value of a phase difference amount in a predetermined range in a plurality of pixels constituting the phase difference image is denoted by $\Phi_0$ and a maximum value thereof is denoted by $\Phi_N$, a peripheral length of an equiphase line in a random phase $\Phi$ in the predetermined range is denoted by $L(\Phi)$, and an area of a region surrounded by an equiphase line having the peripheral length $L(\Phi)$ is denoted by $A(\Phi)$, an average phase fluctuation $\lambda$ defined by the following Equation (3) can be used as the first index value. By using the average phase fluctuation $\lambda$ as the first index value, the randomness of the array of the phase difference amount in a plurality of pixels constituting the phase difference image can be quantified, and therefore, the state of the cells constituting the aggregate can be accurately determined.

In addition, the determination method may include deriving the first index value on the basis of a shape component removal image that has been subjected to a process of removing a component depending on a shape of the aggregate from the phase difference image. For example, an autocorrelation function or a two-dimensional power spectrum derived on the basis of the shape component removal image may be derived as the first index value.

The determination method according to the disclosed technology may include performing a determination related to a survival rate of the cells constituting the aggregate on the basis of the first index value. In addition, in a case where stem cells are the cells constituting the aggregate, the determination method according to the disclosed technology may include performing a determination related to an undifferentiated rate of the stem cells constituting the aggregate on the basis of the first index value. The determination related to the survival rate or the undifferentiated rate of the cells is performed on the basis of the first index value, so that the determination can be performed non-destructively and easily.

The determination method according to the disclosed technology may include deriving a second index value that indicates a correlation between the first index value and a particle diameter of the aggregate for a plurality of the aggregates included in a lot to be determined, and performing a determination for the lot to be determined on the basis of the second index value. This makes it possible to non-destructively and easily determine the lot to be determined.

The determination method according to the disclosed technology may include performing a determination related to a survival rate of the cells included in the lot to be determined on the basis of the second index value. In addition, in a case where stem cells are the cells constituting the aggregate, the determination method according to the disclosed technology may include performing a determination related to an undifferentiated rate of the stem cells included in the lot to be determined on the basis of the second index value. The determination related to the survival rate or the undifferentiated rate of the cells included in the lot to be determined can be performed on the basis of the second index value, so that the determination can be performed non-destructively and easily.

According to the disclosed technology, the state of the aggregate of a plurality of cells formed by three-dimensional culture can be determined non-destructively and easily.

DESCRIPTION OF THE PREFERRED EMBODIMENTS

Figure 1:
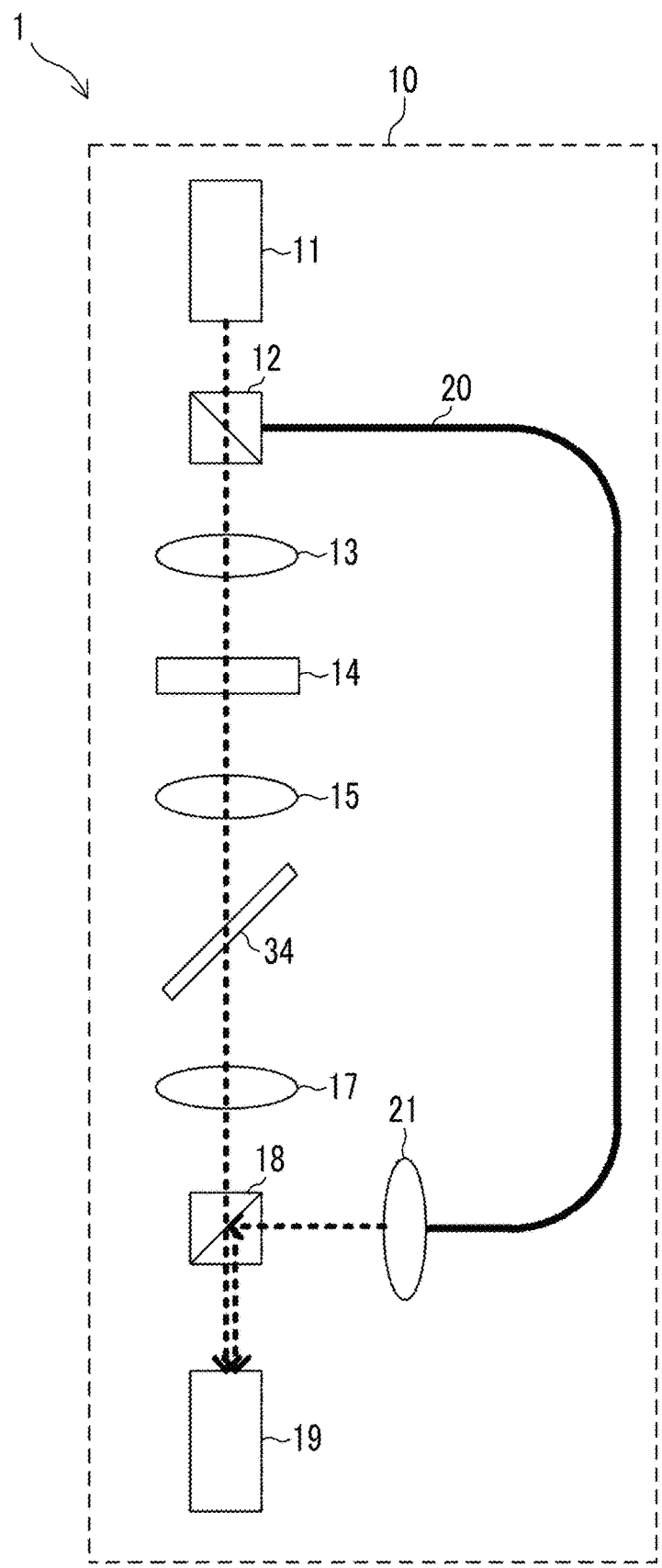
FIG. 1 is a diagram showing an example of a configuration of an imaging system used for performing a determination method according to an embodiment of the disclosed technology.

Hereinafter, embodiments of the present invention will be described with reference to the drawings. In the drawings, substantially the same or equivalent components or portions are denoted by the same reference numerals.

A determination method according to the embodiment of the disclosed technology includes generating a phase difference image of an aggregate (sphere) of a plurality of cells from a hologram obtained by imaging the aggregate (sphere), deriving a first index value that indicates a randomness of an array of a phase difference amount in a plurality of pixels constituting the phase difference image, and determining a state of the cells constituting the aggregate (sphere) on the basis of the first index value. According to this determination method, it is possible to determine the state of the aggregate (sphere) non-destructively and easily.

FIG. 1 is a diagram showing an example of a configuration of an imaging system 1 used for performing a determination method according to an embodiment of the disclosed technology. The imaging system 1 is configured to include a hologram optical system 10 for acquiring the hologram of the sphere using a known digital holography technique.

The digital holography technique is a technique in which an image generated by interference between object light transmitted through or reflected by an object and reference light coherent with the object light is imaged using an image sensor, and numerical calculation based on light propagation is performed on the image obtained by the imaging, thereby restoring a wavefront of a light wave from the object. According to the digital holography technique, it is possible to quantify a phase distribution of the object and acquire three-dimensional information of the object without mechanically moving a focal position.

The hologram optical system 10 is configured to include a laser light source 11, beam splitters 12 and 18, collimating lenses 13 and 21, an objective lens 15, dichroic mirror 34, an imaging lens 17, and a complementary metal oxide semiconductor (CMOS) camera 19. A sphere as a sample 14 set on a sample stage is disposed between the collimating lens 13 and the objective lens 15.

As the laser light source 11, for example, a HeNe laser having a wavelength of 632.8 nm can be used. Laser light emitted from the laser light source 11 is split into two laser lights by the beam splitter 12. One of the two laser lights is object light and the other is reference light. The object light is collimated by the collimating lens 13, and then irradiated onto a sphere as the sample 14 set on the sample stage. An image formed by the object light transmitted through the sphere is magnified by the objective lens 15. The object light transmitted through the objective lens 15 is transmitted through the dichroic mirror 34, is collimated again by the imaging lens 17, and then is formed on an imaging surface of a CMOS camera 19 via the beam splitter 18. On the other hand, the reference light is guided to the front of the collimating lens 21 by the optical fiber 20. The reference light emitted from the optical fiber 20 is collimated by the collimating lens 21 and is incident on the imaging surface of the CMOS camera 19 via the beam splitter 18. The hologram generated by the interference between the object light and the reference light is recorded by the CMOS camera 19. An off-axial optical system in which optical axis directions of the object light and the reference light incident on the imaging surface of the CMOS camera 19 are different from each other may be configured.

According to the imaging system 1 according to the present embodiment, it is possible to acquire a phase difference image of the sphere without destroying the sphere and without damaging the cells constituting the sphere. The configuration of the above-described imaging system 1 is merely an example, and the present invention is not limited to the above-described configuration. Any imaging system capable of acquiring a hologram using digital holography technique can be used to perform the determination method according to the disclosed technology.

Hereinafter, an example of a method of acquiring a phase difference image of a sphere from a hologram of the sphere acquired by using the imaging system 1 will be described.

Figure 2A:
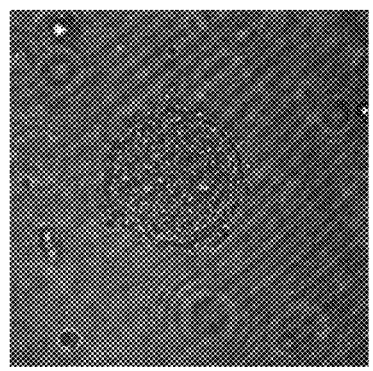
FIG. 2A is a diagram showing an example of a hologram used for performing a determination method according to an embodiment of the disclosed technology.
Figure 2B:
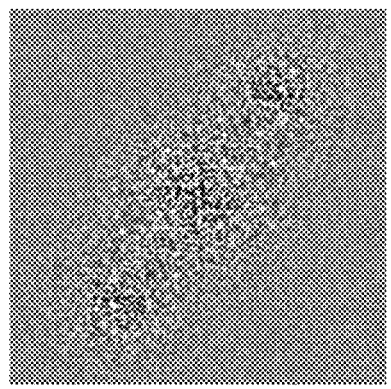
FIG. 2B is a diagram showing an example of a Fourier transform image of a sphere.

First, the hologram exemplified in FIG. 2A acquired by the CMOS camera 19 is subjected to a two-dimensional Fourier transform to extract a complex amplitude component of only the object light. FIG. 2B is an example of a Fourier transform image of the sphere obtained by this process.

Figure 2C:
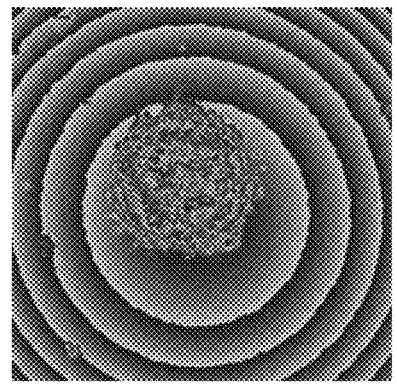
FIG. 2C is a diagram showing an example of a phase difference image of a sphere before unwrapping.
Figure 2D:
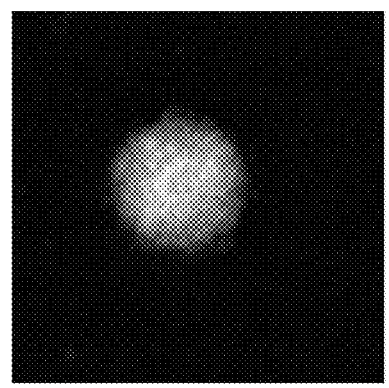
FIG. 2D is a diagram showing an example of a phase difference image of a sphere after unwrapping.

Next, for example, the angular spectrum method is applied to restore the image showing the phase of the sphere at an arbitrary spatial position. FIG. 2C is an example of a phase difference image before unwrapping of the sphere obtained by this process. The phase of the sphere at this point is convolved with a value of 0 to $2\pi$. Therefore, for example, by applying a phase connection (unwrapping) method such as unweighted least squares or Flynn's algorithm to join portions of $2\pi$ or more, a final phase difference image of the sphere as exemplified in FIG. 2D can be obtained. It should be noted that many unwrapping methods have been proposed, and an appropriate method that does not cause phase mismatch may be appropriately selected.

Figure 3:
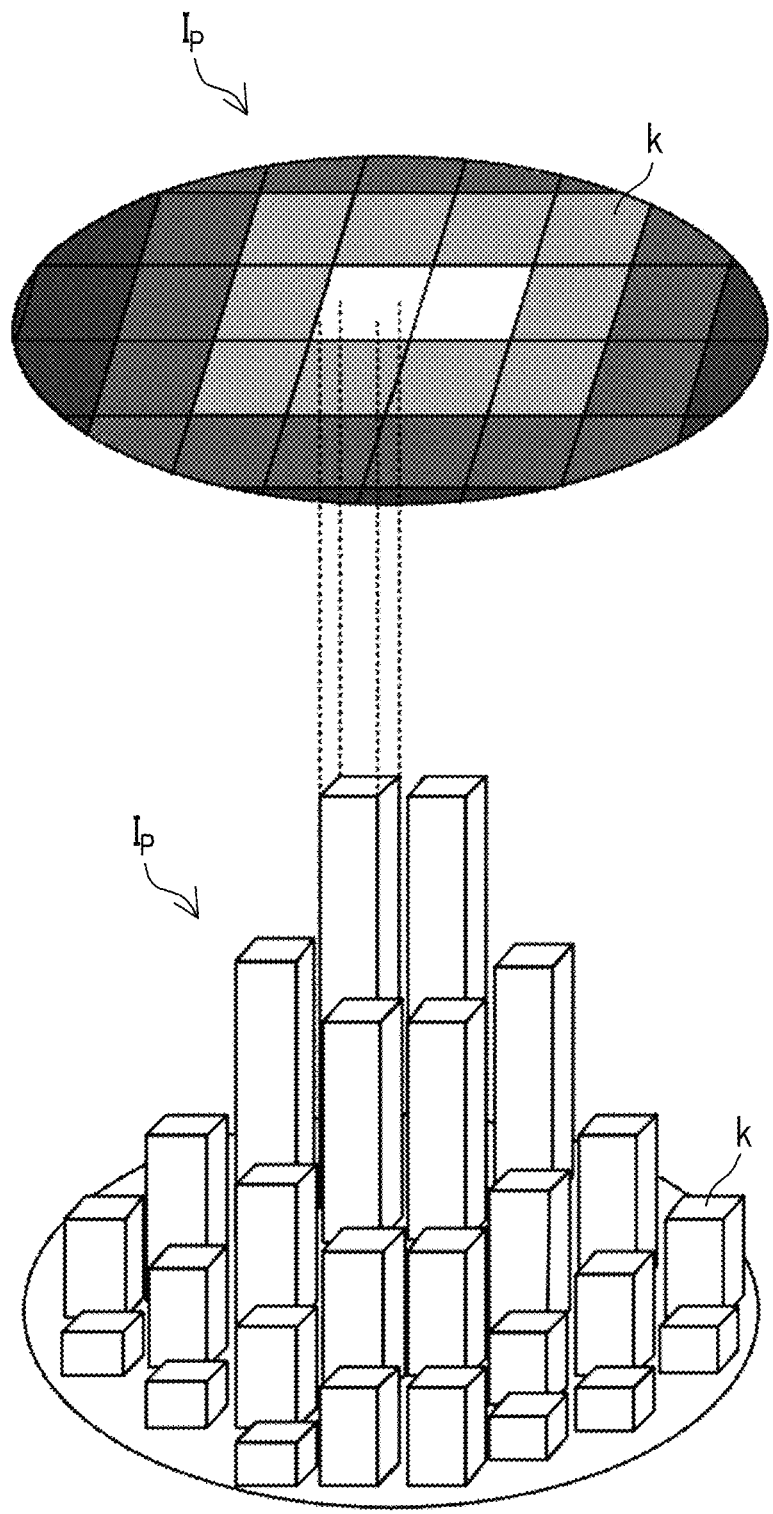
FIG. 3 is a diagram showing the concept of a phase difference image according to an embodiment of the disclosed technology.

FIG. 3 is a diagram showing the concept of a phase difference image $I_P$. The lower part of FIG. 3 is an image in which a phase difference amount at each pixel k of the phase difference image $I_P$ is three-dimensionally displayed. The upper part of FIG. 3 is a diagram showing the phase difference amount at each pixel k of the phase difference image $I_P$ on a plane in gray scale.

Here, a phase difference amount $\theta$ in the phase difference image $I_P$ is represented by the following Equation (1) in a case where $\theta_B$ is a phase of a background (region where the sphere does not exist) existing in the same focal plane of the phase difference image $I_P$, and $\theta_S$ is a phase of a region where the sphere exists. In addition, the term "phase" in the present specification is a phase of an electric field amplitude in a case where light is regarded as an electromagnetic wave, and is used in a more general sense.

$$\theta = \theta_S - \theta_B \qquad (1)$$

In addition, a phase difference amount $\theta_k$ at each pixel k of the phase difference image $I_P$ can be represented by the following Equation (2). Here, $n_k$ is refractive index of the sphere at the portion corresponding to each pixel k of the phase difference image $I_P$, $d_k$ is a thickness of the sphere at the portion corresponding to each pixel k of the phase difference image $I_P$, and $\lambda$ is a wavelength of the object light in the hologram optical system 10.

$$\theta_k = 2\pi n_k \cdot d_k / \lambda \qquad (2)$$

The phase difference image of the sphere is an image showing an optical path length distribution of the object light transmitted through the sphere. Since the optical path length in the sphere corresponds to the product of the refractive index of the sphere and the thickness of the sphere, the phase difference image of the sphere includes information on the refractive index and the thickness (shape) of the sphere, as also shown in Equation (2).

Accurate information matching the actual condition of the sphere cannot be obtained from the phase difference image that is out of focus with respect to the sphere by the influence of the spread due to diffraction. Therefore, it is preferable to focus on the sphere in a case of acquiring the phase difference image from the hologram acquired by the CMOS camera 19. Here, "focusing on a sphere" means obtaining a phase difference image sliced near a center of a spherical sphere. A more accurate determination result can be obtained by determining the state of the sphere using the phase difference image focused on the sphere.

It is preferable to automate the focusing of the phase difference image without manual operation. By automating the focusing, it is possible to eliminate the arbitrariness by an operator and further shorten the processing time. The inventors have found an automatable focusing technique described below.

Figure 4:
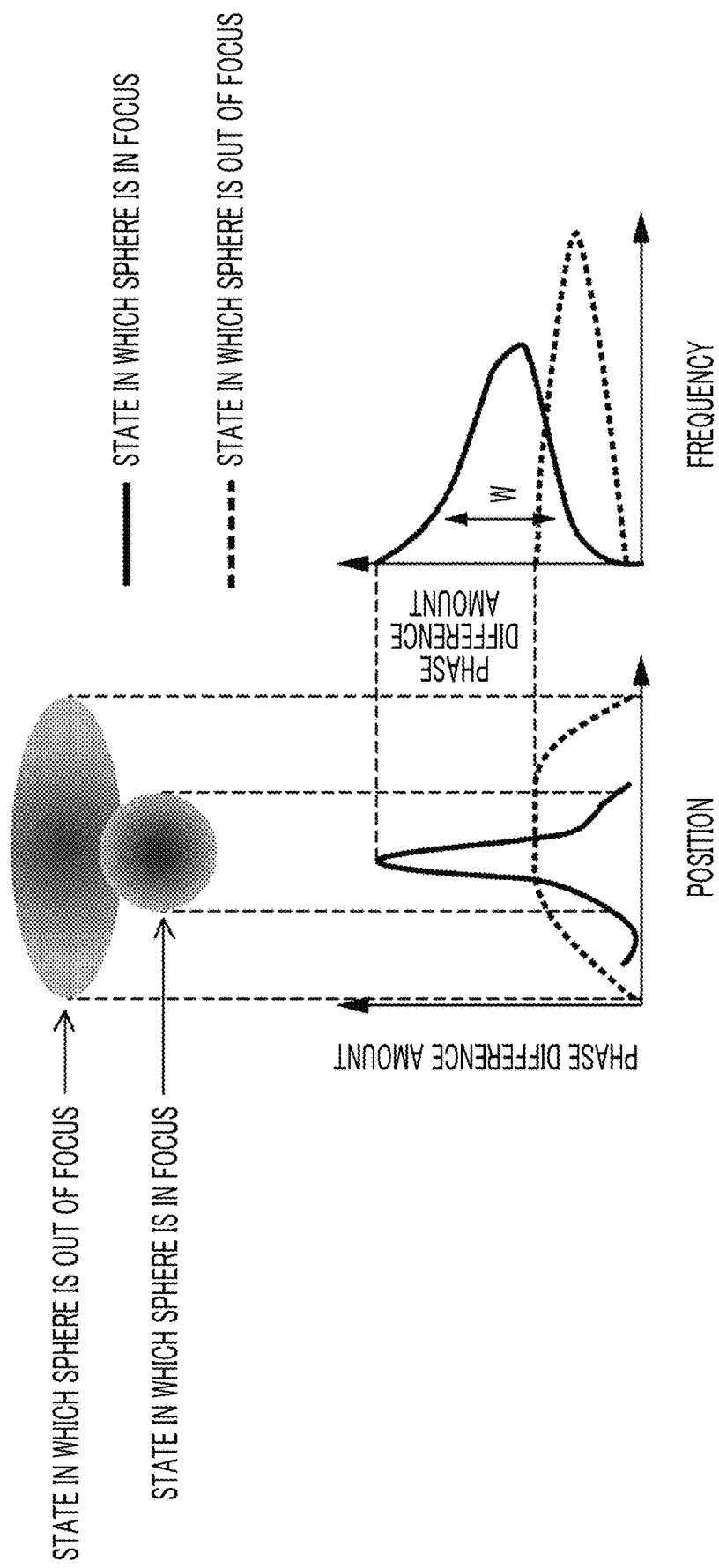
FIG. 4 is an explanatory diagram related to focusing of a phase difference image according to an embodiment of the disclosed technology.

The graph on the left side of FIG. 4 is a graph showing an example of a relationship between the position of the sphere in the plane direction and the phase difference amount in the phase difference image, in which a solid line corresponds to a state in which the sphere is in focus and a dotted line corresponds to a state in which the sphere is out of focus. In a case where the sphere is in focus, a steep peak appears at a specific position in the phase difference image. On the other hand, in a case where the sphere is out of focus, the peak is lower and smoother than the case where the sphere is in focus.

The graph on the right side of FIG. 4 is an example of a histogram of the phase difference amount in the phase difference image of the sphere, in which a solid line corresponds to a state in which the sphere is in focus and a dotted line corresponds to a state in which the sphere is out of focus. In the case where the sphere is in focus, a half-width w of a curve (variation in the phase difference amount) is relatively large, and in the case where the sphere is out of focus, the half-width w of the curve (variation in the phase difference amount) is relatively small.

Therefore, focusing can be realized by acquiring phase difference image of the sphere for each of different focal positions (slice positions), obtaining the half-width w of the curve in the histogram of the phase difference amount (variation in the phase difference amount) for each of the acquired phase difference image, and extracting the phase difference image having the maximum half-width w among the obtained half-widths w as the phase difference image focused on the sphere.

Figure 5:
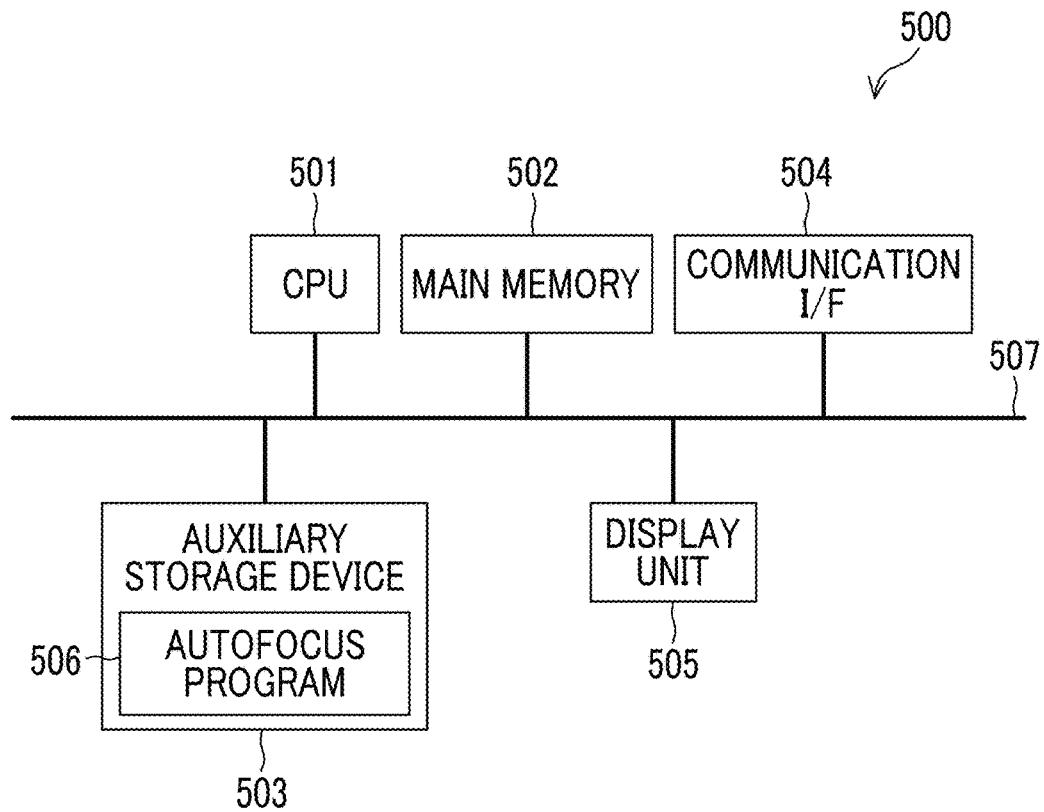
FIG. 5 is an example of a hardware configuration of a computer that performs an autofocus processing according to an embodiment of the disclosed technology.

The above-described focusing can be automated using a computer. FIG. 5 is an example of a hardware configuration of a computer 500 that performs an autofocus processing of automatically performing the above-described focusing.

The computer 500 includes a central processing unit (CPU) 501, a main memory 502 as a temporary storage region, a nonvolatile auxiliary storage device 503, a communication interface (I/F) 504 for communicating with the CMOS camera 19, and a display unit 505 such as a liquid crystal display. The CPU 501, the main memory 502, the auxiliary storage device 503, the communication I/F 504, and the display unit 505 are each connected to a bus 507. The auxiliary storage device 503 houses an autofocus program 506 which describes the procedure of the above-described autofocus processing. In the computer 500, the CPU 501 executes the autofocus program 506 to perform the autofocus processing.

Figure 6:
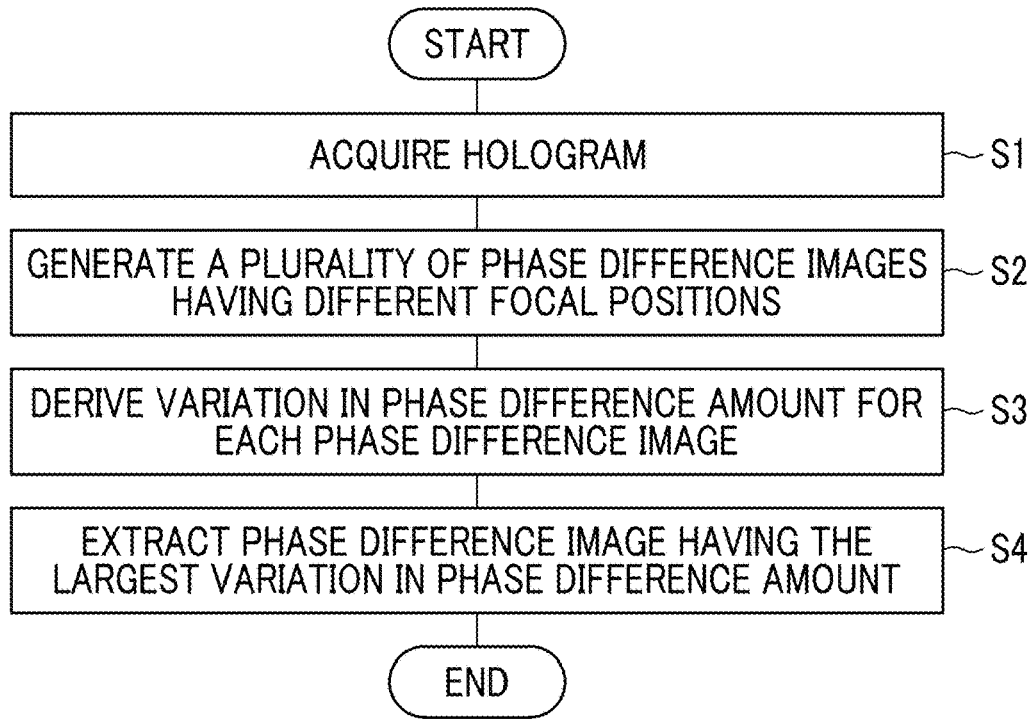
FIG. 6 is a flowchart showing an example of a flow of an autofocus processing according to an embodiment of the disclosed technology.

FIG. 6 is a flowchart showing an example of a flow of the autofocus processing performed by the computer 500.

In step S1, the CPU 501 acquires a hologram of the sphere from the CMOS camera 19.

In step S2, the CPU 501 generates a plurality of phase difference images having different focal positions (slice positions) from the acquired hologram.

In step S3, the CPU 501 derives the variation in the phase difference amount for each phase difference image for each focal position (slice position). For example, the CPU 501 may derive a difference between the maximum value and the minimum value of the phase difference amount in the phase difference image as the variation of the phase difference amount in the phase difference image.

In step S4, the CPU 501 extracts a phase difference image having the largest variation in the phase difference amount derived in step S3 as the phase difference image focused on the sphere among the plurality of phase difference images having different focal positions (slice positions).

Figure 7:
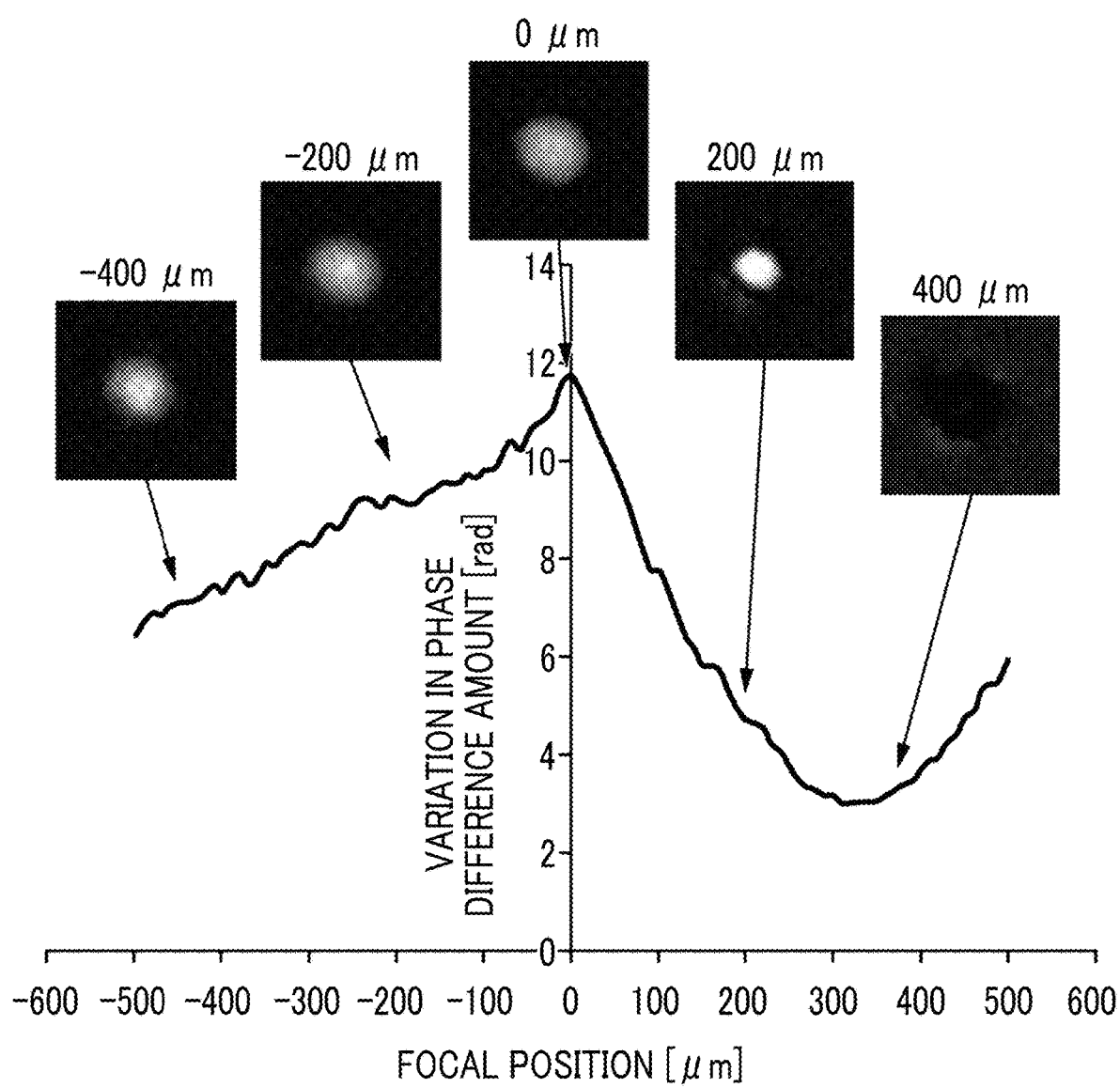
FIG. 7 is a graph showing an example of a relationship between a focal position and variation in a phase difference amount in a phase difference image of a sphere according to an embodiment of the disclosed technology.

FIG. 7 is a graph showing an example of the relationship between the focal position (slice position) and the variation in the phase difference amount in the phase difference image of the sphere. In FIG. 7, phase difference images of spheres corresponding to focal positions of −400 μm, −200 μm, 0 μm, +200 μm, and +400 μm are exemplified with a graph. In FIG. 7, a focal position in which the variation in the phase difference amount is the maximum is set to 0 μm. According to the above-described autofocus processing, the phase difference image corresponding to the focal position 0 μm in which the variation in the phase difference amount is the maximum is extracted as the focused phase difference image. In the phase difference image corresponding to the focal position 0 μm in which the variation of the phase difference amount is maximum, a contour of the sphere is the clearest.

As described above, the determination method according to the embodiment of the disclosed technology includes deriving a first index value that indicates a randomness of an array of a phase difference amount in a plurality of pixels constituting the phase difference image, and determining a state of the cells constituting the sphere on the basis of the first index value.

Figure 8A:
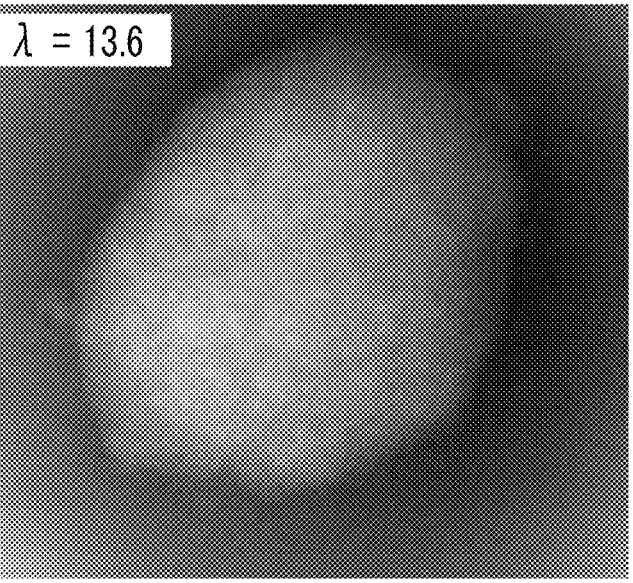
FIG. 8A is a diagram showing a phase difference image of a sphere.
Figure 8B:
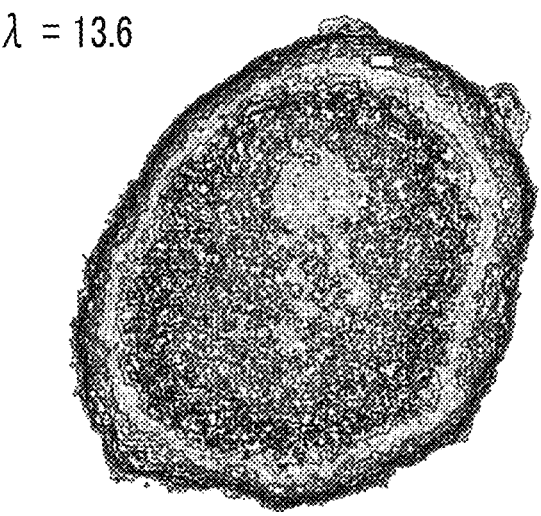
FIG. 8B is a contour diagram showing a distribution of a phase difference amount in the phase difference image shown in FIG. 8A.
Figure 9A:
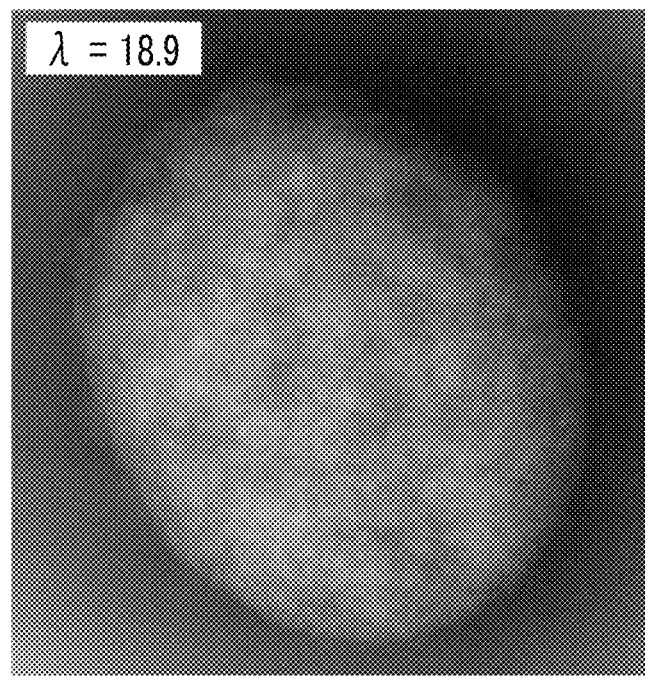
FIG. 9A is a diagram showing a phase difference image of a sphere.
Figure 9B:
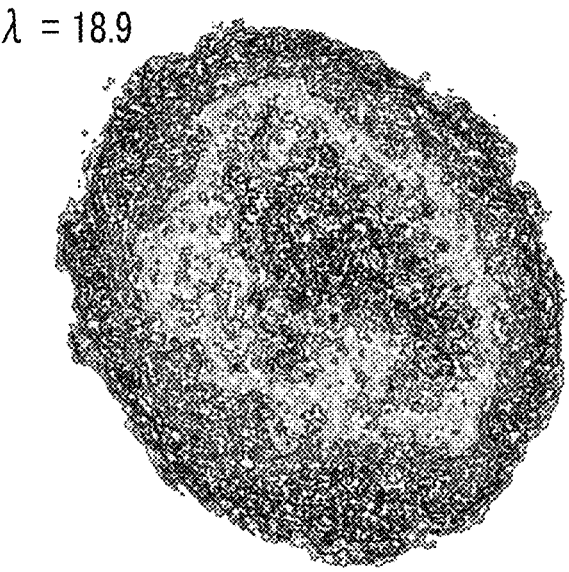
FIG. 9B is a contour diagram showing a distribution of a phase difference amount in the phase difference image shown in FIG. 9A.

FIG. 8A is a diagram showing a representative example of the phase difference image of the spheres which are aggregates of iPS cells extracted from a culture lot in which a ratio (hereinafter referred to as undifferentiated rate) of the iPS cells maintaining an undifferentiated state within the lot is 99%. FIG. 8B is a contour diagram showing a distribution of the phase difference amount in the phase difference image shown in FIG. 8A. FIG. 9A is a diagram showing a representative example of the phase difference image of the spheres which are aggregates of iPS cells extracted from a culture lot in which the undifferentiated rate is 87%. FIG. 9B is a contour diagram showing the distribution of the phase difference amount in the phase difference image shown in FIG. 9A.

A sphere within a lot with a relatively high undifferentiated rate (that is, differentiation into germ layers is progressing) is considered to have higher internal homogeneity than a sphere within a lot with a relatively low undifferentiated rate. Therefore, in the phase difference image of the sphere within the lot having a relatively high undifferentiated rate, as shown in FIG. 8B, a shape of a region surrounded by an equiphase line connecting the pixels having the same phase difference amount is nearly circular, and the equiphase line is concentrically distributed. On the other hand, in a phase difference image of a sphere within a lot having a relatively low undifferentiated rate, as shown in FIG. 9B, the array of the phase difference amount in a plurality of pixels constituting the phase difference image is random, and the shape of the region surrounded by the equiphase line is distorted. That is, a progress state of differentiation of the cells constituting the sphere is reflected in the randomness of the array of the phase difference amount in a plurality of pixels constituting the phase difference image of the sphere. Therefore, it is possible to quantify the progress state of the differentiation of the cells constituting the sphere by the index value indicating the randomness of the array of the phase difference amount in a plurality of pixels constituting the phase difference image of the sphere.

As the index value indicating the randomness of the array of the phase difference amounts in a plurality of pixels constituting the phase difference image of the sphere, for example, the index value determined according to a degree of deviation from a circle of the shape of the region surrounded by the equiphase line connecting the pixels of the same phase difference amount in the phase difference image of the sphere can be used.

Specifically, an average phase fluctuation λ defined by the following Equation (3) can be used as the index value indicating the randomness of the array of the phase difference amounts in a plurality of pixels constituting the phase difference image of the sphere. In the following Equation (3), $\Phi_0$ is the minimum value of the phase difference amount in a predetermined range in a plurality of pixels constituting the phase difference image, and $\Phi_N$ is the maximum value of the phase difference amount in the predetermined range. L (Φ) is a peripheral length of the equiphase line at a random phase Φ within the predetermined range, and A (Φ) is the area of the region surrounded by the equiphase line of the peripheral length L (Φ).

$$\lambda = \frac{1}{\Phi_N - \Phi_0} \int_{\Phi_0}^{\Phi_N} \frac{L(\Phi)^2}{4\pi A(\Phi)} d\Phi \qquad (3)$$

The average phase fluctuation λ is the minimum in a case where the shape of the region surrounded by the equiphase line is a perfect circle, and increases as the shape of the region surrounded by the equiphase line deviates from the circle. That is, the higher the randomness of the shape of the region surrounded by the equiphase line, the larger the average phase fluctuation λ.

As shown in FIG. 8A and FIG. 8B, the average phase fluctuation λ in the phase difference image of the sphere corresponding to the undifferentiated rate of 99% is 13.6, and as shown in FIG. 9A and FIG. 9B, the average phase fluctuation λ in the phase difference image of the sphere corresponding to the undifferentiated rate of 87% is 18.9. The sphere within the lot having the relatively low undifferentiated rate includes a plurality of cells deviating from the undifferentiated state, thereby reducing the homogeneity inside the sphere. As a result, the randomness of the array of the phase difference amounts in a plurality of pixels constituting the phase difference image of the sphere is increased, and the average phase fluctuation λ is increased.

In this way, by using the average phase fluctuation λ as the index value indicating the randomness of the array of the phase difference amounts in a plurality of pixels constituting the phase difference image of the sphere, the progress state of differentiation of the cells constituting the sphere can be estimated without destroying the cells.

Figure 10A:
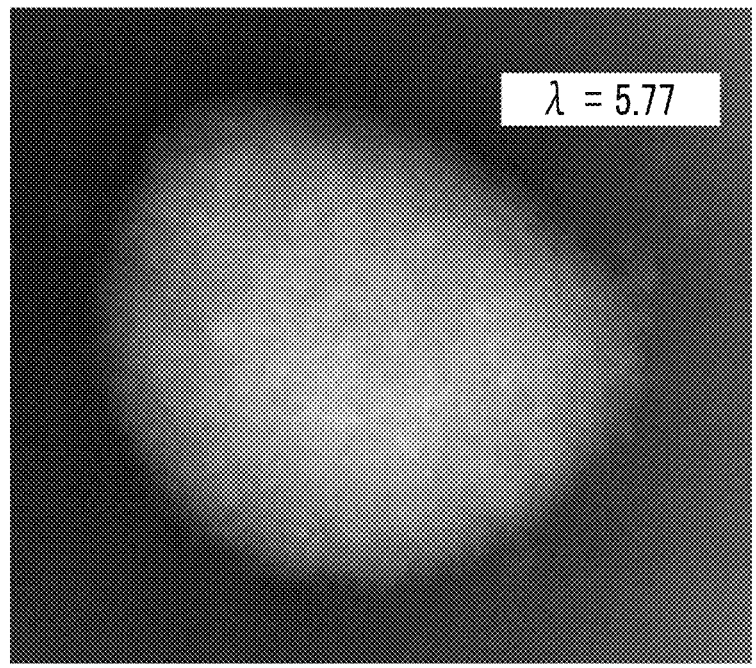
FIG. 10A is a diagram showing a phase difference image of a sphere.
Figure 10B:
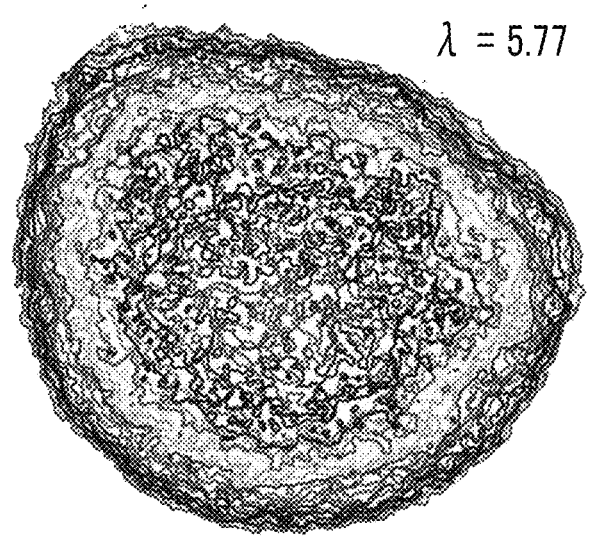
FIG. 10B is a contour diagram showing a distribution of a phase difference amount in the phase difference image shown in FIG. 10A.
Figure 11A:
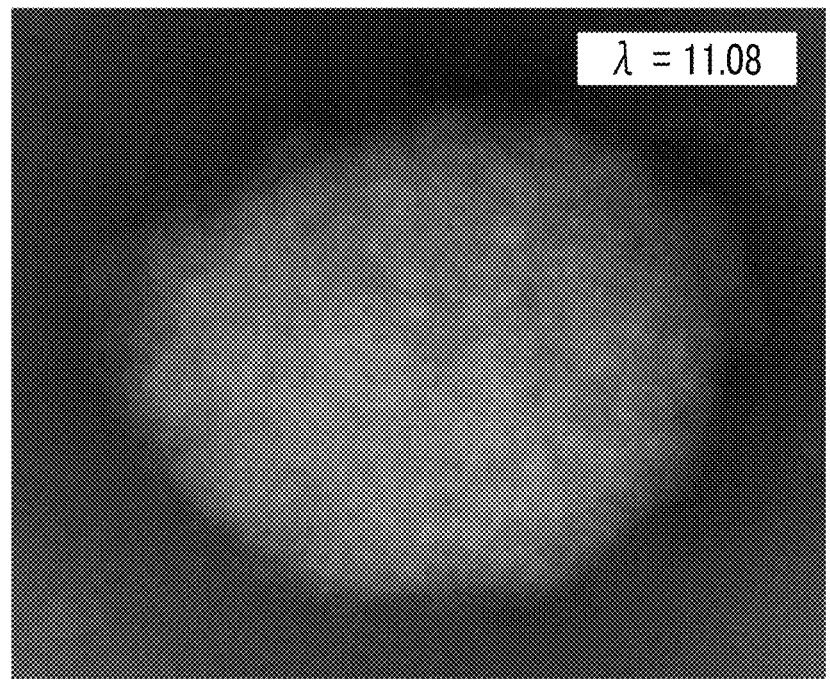
FIG. 11A is a diagram showing a phase difference image of a sphere.
Figure 11B:
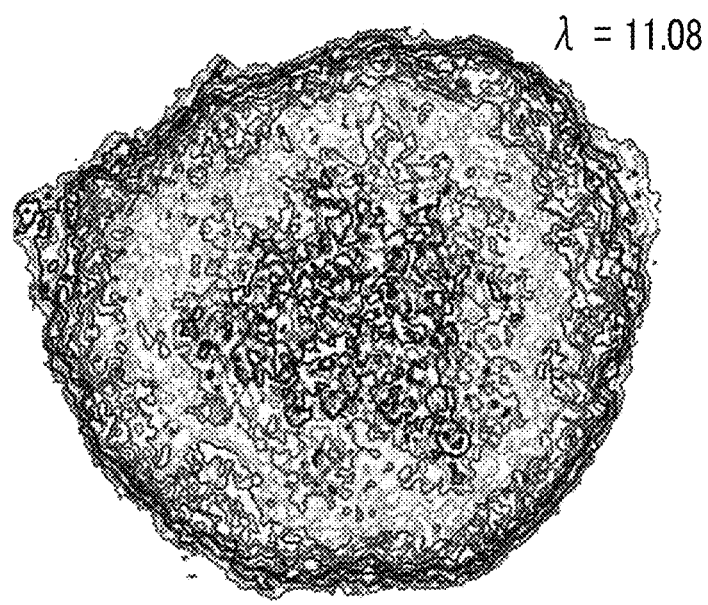
FIG. 11B is a contour diagram showing a distribution of a phase difference amount in the phase difference image shown in FIG. 11A.

The average phase fluctuation λ can be used not only for determining the progress state of the differentiation of the cells but also for determining a survival rate of cells in the sphere. FIG. 10A is a diagram showing a representative example of a phase difference image of spheres which are aggregates of iPS cells extracted from a lot having a survival rate of cells of 87.3% within the lot. FIG. 10B is a contour diagram showing the distribution of the phase difference amount in the phase difference image shown in FIG. 10A. FIG. 11A is a diagram showing a representative example of a phase difference image of spheres which are aggregates of iPS cells extracted from a culture lot having a survival rate of cells of 59.2% within the lot. FIG. 11B is a contour diagram showing the distribution of the phase difference amount in the phase difference image shown in FIG. 11A.

Healthy cells are considered to maintain a constant internal refractive index different from the refractive index of the medium due to their homeostasis. On the other hand, it is considered that dead cells lose homeostasis and the internal refractive index is almost the same as that of the medium. Accordingly, spheres in a culture lot having relatively high survival rate of cells are considered to have higher internal homogeneity than spheres within a culture lot having relatively low survival rate of cells. Therefore, in the phase difference image of the sphere within the culture lot having a relatively high survival rate of cells, as shown in FIG. 10B, a shape of a region surrounded by an equiphase line connecting the pixels having the same phase difference amount is nearly circular, and the equiphase line is concentrically distributed. On the other hand, in a phase difference image of a sphere within the culture lot having a relatively low survival rate of cells, as shown in FIG. 11B, the array of the phase difference amount in a plurality of pixels constituting the phase difference image is random, and the shape of the region surrounded by the equiphase line is distorted. That is, the survival rate of cells constituting the sphere is reflected in the randomness of the array of the phase difference amount in a plurality of pixels constituting the phase difference image of the sphere. Therefore, the average phase fluctuation λ can be used to determine the survival rate of cells in the sphere.

As shown in FIG. 10A and FIG. 10B, the average phase fluctuation λ in the phase difference image of the sphere corresponding to the survival rate of cells of 87.3% is 5.77, and as shown in FIG. 11A and FIG. 11B, the average phase fluctuation λ in the phase difference image of the sphere corresponding to the survival rate of cells of 59.2% is 11.08. The sphere within the lot having the relatively low survival rate of cells includes many dead cells inside, thereby reducing the homogeneity inside the sphere. As a result, the randomness of the array of the phase difference amounts in a plurality of pixels constituting the phase difference image of the sphere is increased, and the average phase fluctuation λ is increased.

In this way, by using the average phase fluctuation λ as the index value indicating the randomness of the array of the phase difference amounts in a plurality of pixels constituting the phase difference image of the sphere, the survival rate of cells constituting the sphere can be estimated without destroying the cells.

The determination method according to the embodiment of the disclosed technology may include deriving the second index value indicating a correlation between the index value (hereinafter, referred to as the first index value) indicating randomness of the array of the phase difference amounts in a plurality of pixels constituting the phase difference image of the sphere and the sphere particle diameter with respect to a plurality of spheres included in the lot to be determined, and performing a determination for the lot to be determined on the basis of the second index value. As the first index value, the average phase fluctuation λ can be used.

Figure 12:
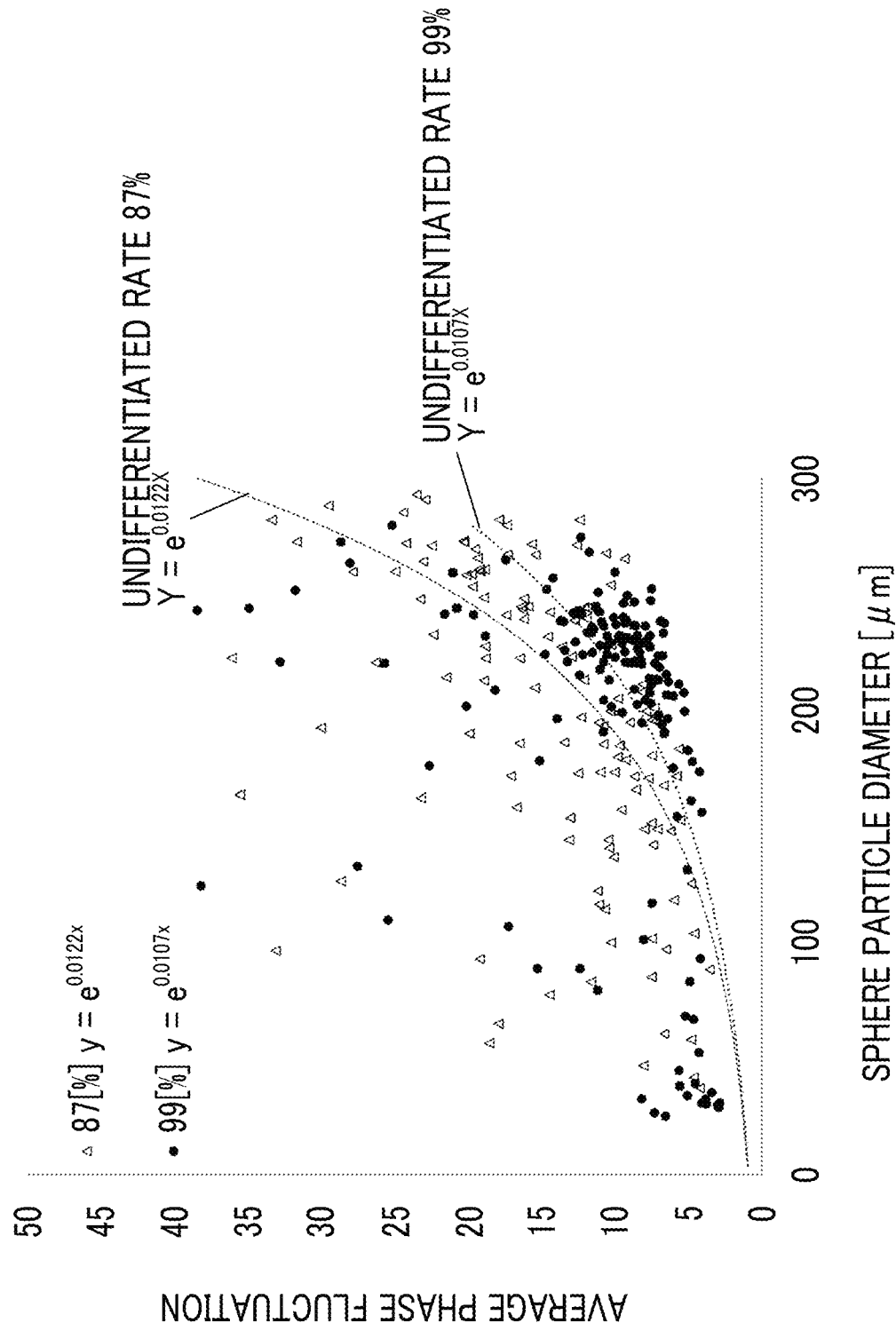
FIG. 12 is a graph showing an example of a correlation between a sphere particle diameter and an average phase fluctuation.

FIG. 12 is a graph showing the correlation between the sphere particle diameter and the average phase fluctuation λ acquired for a plurality of spheres included in each of two lots having undifferentiated rates of 87% and 99%, respectively. As shown in FIG. 12, it is found that as the sphere particle diameter increases, there is a tendency that the average phase fluctuation λ increases. Sphere particle diameter dependency of the average phase fluctuation λ can be considered to represent the characteristics of a cell line, and the characteristic of a three-dimensional culture process and a differentiation induction process. Specifically, due to a gas density and a permeability of the inducing factor, a sphere having a small particle diameter tends to be uniform in the progress of differentiation, while a sphere having a large particle diameter tends to be uneven in the progress of differentiation, and size density of a cell density in the sphere is different according to the culture and/or differentiation induction process. Accordingly, it is considered that such factors cause the average phase fluctuation λ to have the sphere particle diameter dependency.

In addition, as shown in FIG. 12, it is found that there is a difference in the correlation between the sphere particle diameter and the average phase fluctuation λ between the lot having the undifferentiated rate of 87% and the lot having the undifferentiated rate of 99%. That is, the difference in the undifferentiated rate between lots is reflected in the correlation between the sphere particle diameter and the average phase fluctuation λ. The correlation between the sphere particle diameter and the average phase fluctuation λ exemplified in FIG. 12, for example, can be fitted by the function shown in the following Equation (4). That is, the correlation between the sphere particle diameter and the average phase fluctuation λ can be represented by an approximate equation by the function shown in the following Equation (4). In the following Equation (4), X is a sphere particle diameter, Y is the average phase fluctuation λ, and A is a constant. In the following Equation (4), the constant A can be used as the index value (the second index value) indicating the correlation (characterizing the correlation) between the sphere particle diameter and the average phase fluctuation λ.

$$Y=e^{AX} \qquad (4)$$

The correlation between the sphere particle diameter and the average phase fluctuation λ in the lot of the undifferentiated rate of 87% shown in FIG. 12 can be represented as $Y=e^{0.0122X}$ by fitting according to the function of Equation (4). That is, the constant A, which is the index value (the second index value) that characterizes the correlation between the sphere particle diameter and the average phase fluctuation λ in the lot having the undifferentiated rate of 87%, is 0.0122. In addition, the correlation between the sphere particle diameter and the average phase fluctuation λ in the lot of the undifferentiated rate of 99% shown in FIG. 12 can be represented as $Y=e^{0.0107X}$ by fitting according to the function of Equation (4). That is, the constant A, which is the index value (the second index value) that characterizes the correlation between the sphere particle diameter and the average phase fluctuation λ in the lot having the undifferentiated rate of 99%, is 0.0107.

Figure 13:
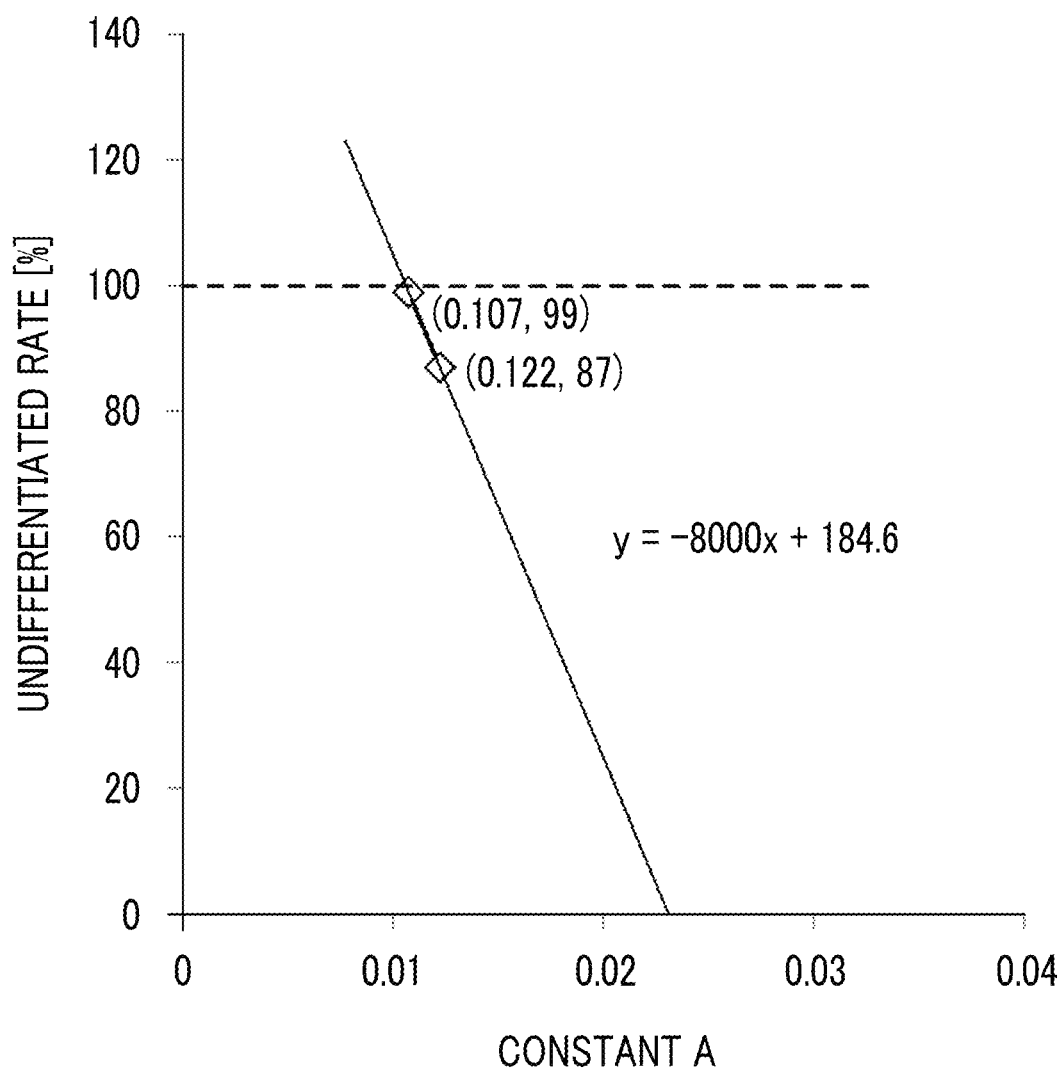
FIG. 13 is a graph showing an example of a correlation between a constant A and an undifferentiated rate.

FIG. 13 is a graph showing the correlation between the constant A of Equation (4) and the undifferentiated rate in the two lots shown in FIG. 12 having different undifferentiated rates. As shown in FIG. 13, since there is a certain correlation between the constant A and the undifferentiated rate, it is possible, for example, to estimate the undifferentiated rate of cells in the lot to be determined on the basis of the constant A. As described above, the undifferentiated rate can be estimated for the lot to be determined on the basis of the constant A (the second index value) which is the index value indicating the correlation between the average phase fluctuation λ (the first index value) and the sphere particle diameter, and the quality determination of the lot to be determined can be performed, for example, on the basis of the estimated undifferentiated rate.

Figure 14:
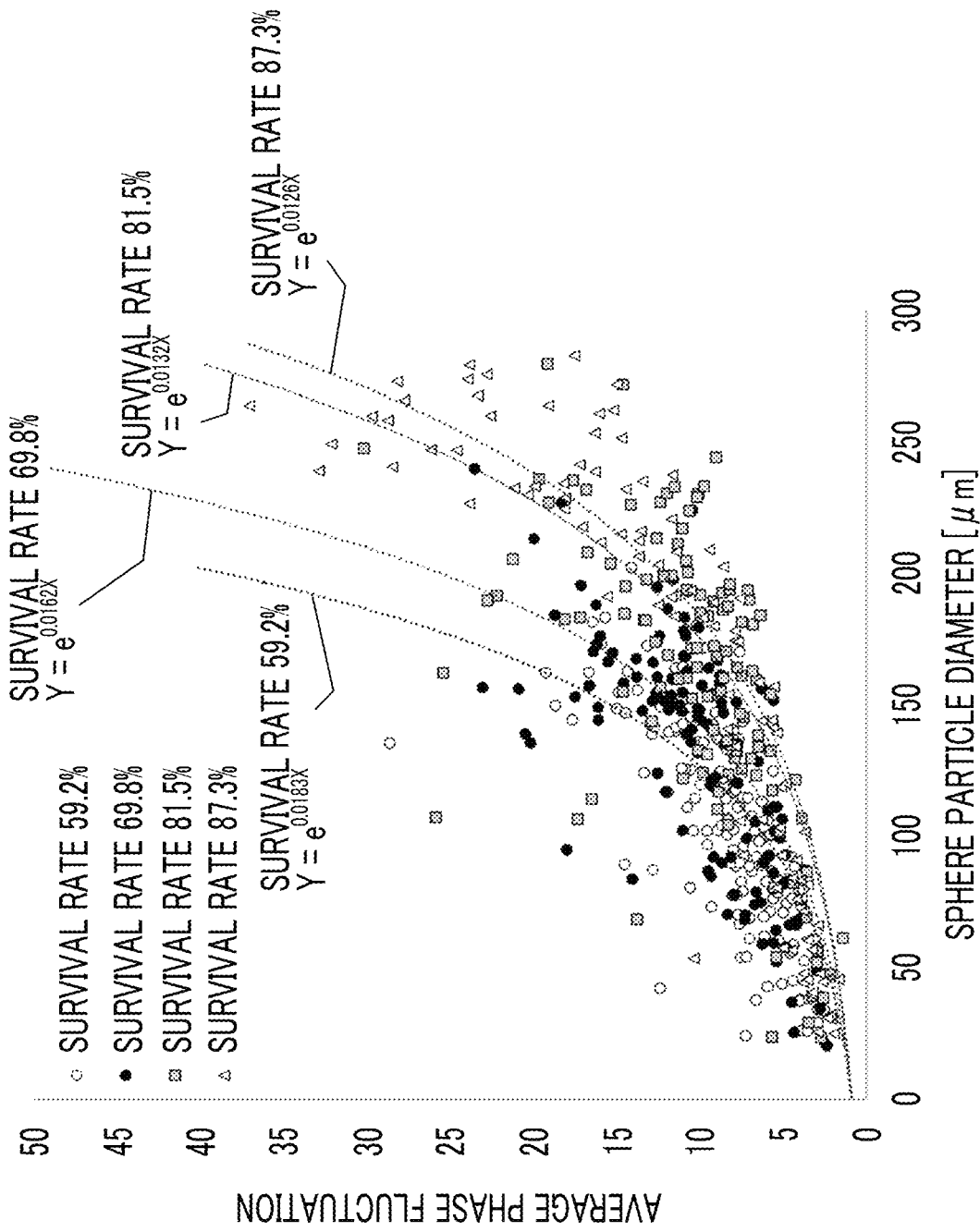
FIG. 14 is a graph showing an example of a correlation between a sphere particle diameter and an average phase fluctuation.

FIG. 14 is a graph showing the correlation between the sphere particle diameter and the average phase fluctuation λ acquired for a plurality of spheres included in each of four lots having the survival rate of cells in the lot of 59.2%, 69.8%, 81.5%, and 87.3%, respectively. As described above, the average phase fluctuation λ has a sphere particle diameter dependency. As shown in FIG. 14, it is found that there is a difference in the correlation between the sphere particle diameter and the average phase fluctuation λ between lots having different survival rates. That is, the difference in the survival rate of cells between lots is reflected in the correlation between the sphere particle diameter and the average phase fluctuation λ. The correlation between the sphere particle diameter and the average phase fluctuation λ shown in FIG. 14, for example, can be fitted by the function shown in Equation (4). That is, the correlation between the sphere particle diameter and the average phase fluctuation λ can be represented by an approximate equation by the function shown in the following Equation (4).

The correlation between the sphere particle diameter and the average phase fluctuation λ in the lot of the survival rate of 59.2% shown in FIG. 14 can be represented as $Y=e^{0.0183X}$ by fitting according to the function of Equation (4). That is, the constant A, which is the index value (the second index value) that characterizes the correlation between the sphere particle diameter and the average phase fluctuation λ in the lot having the survival rate of 59.2%, is 0.0183. In addition, the correlation between the sphere particle diameter and the average phase fluctuation λ in the lot of the survival rate of 69.8% shown in FIG. 14 can be represented as $Y=e^{0.0162X}$ by fitting according to the function of Equation (4). That is, the constant A, which is the index value (the second index value) that characterizes the correlation between the sphere particle diameter and the average phase fluctuation λ in the lot having the survival rate of 69.8%, is 0.0162. The correlation between the sphere particle diameter and the average phase fluctuation λ in the lot of the survival rate of 81.5% shown in FIG. 14 can be represented as $Y=e^{0.0132X}$ by fitting according to the function of Equation (4). That is, the constant A, which is the index value (the second index value) that characterizes the correlation between the sphere particle diameter and the average phase fluctuation λ in the lot having the survival rate of 81.5%, is 0.0132. In addition, the correlation between the sphere particle diameter and the average phase fluctuation λ in the lot of the survival rate of 87.3% shown in FIG. 14 can be represented as $Y=e^{0.0126X}$ by fitting according to the function of Equation (4). That is, the constant A, which is the index value (the second index value) that characterizes the correlation between the sphere particle diameter and the average phase fluctuation λ in the lot having the survival rate of 87.3%, is 0.0126.

Figure 15:
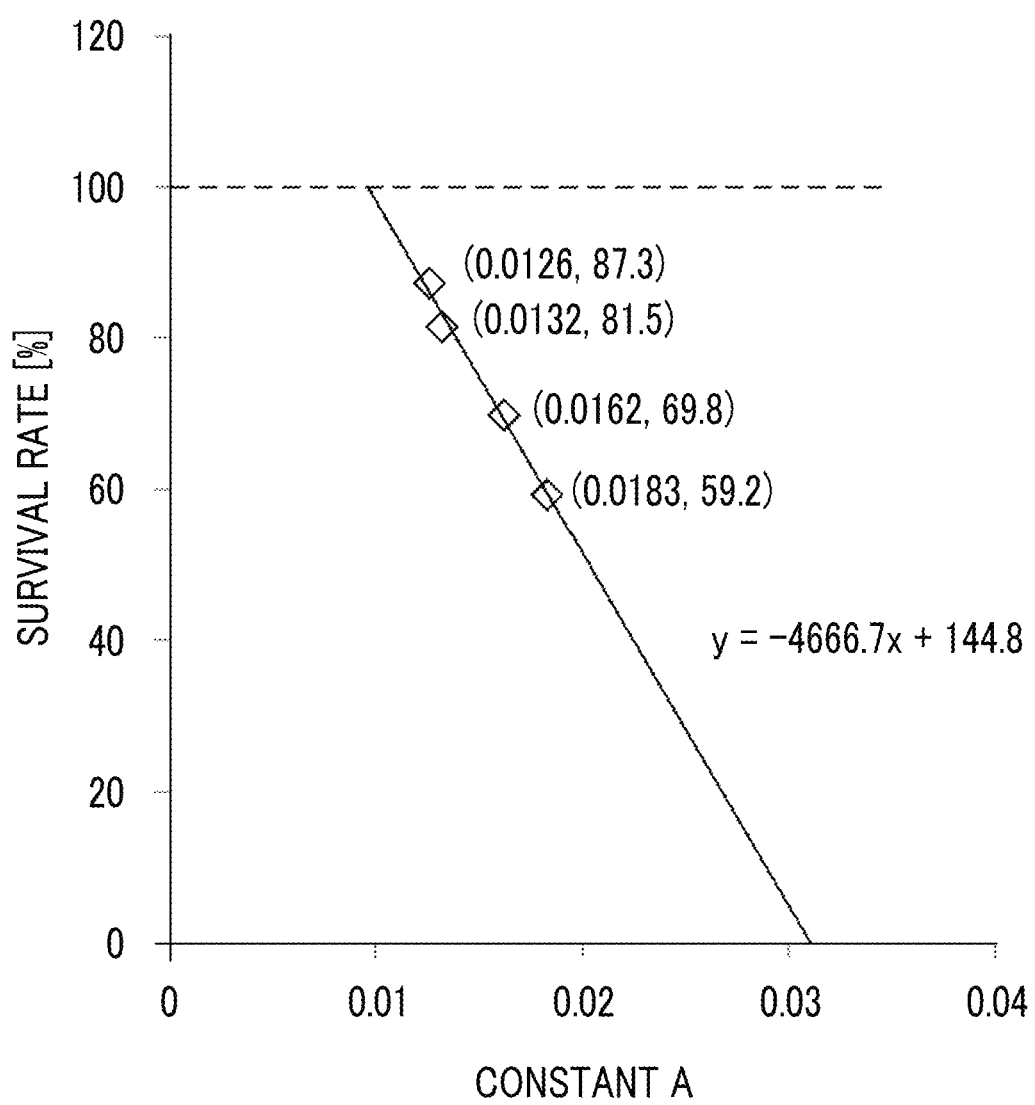
FIG. 15 is a graph showing a correlation between a constant A and a survival rate of cells.

FIG. 15 is a graph showing the correlation between the constant A of Equation (4) and the survival rate of cells in the four lots shown in FIG. 14 having different survival rate of cells. As shown in FIG. 15, since there is a certain correlation between the constant A and the survival rate of cells, it is possible to estimate the survival rate of cells within the lot to be determined on the basis of the constant A. As described above, the survival rate of cells within the lot can be estimated for the lot to be determined on the basis of the constant A (the second index value) which is the index value indicating the correlation between the average phase fluctuation λ (the first index value) and the sphere particle diameter, and the quality determination of the lot to be determined can be performed, for example, on the basis of the estimated survival rate of cells.

In the above description, the case where the average phase fluctuation λ defined by Equation (3) is used as the index value indicating the randomness of the array of the phase difference amounts in a plurality of pixels constituting the phase difference image of the sphere is exemplified, but the present invention is not limited to this aspect.

Figure 16:
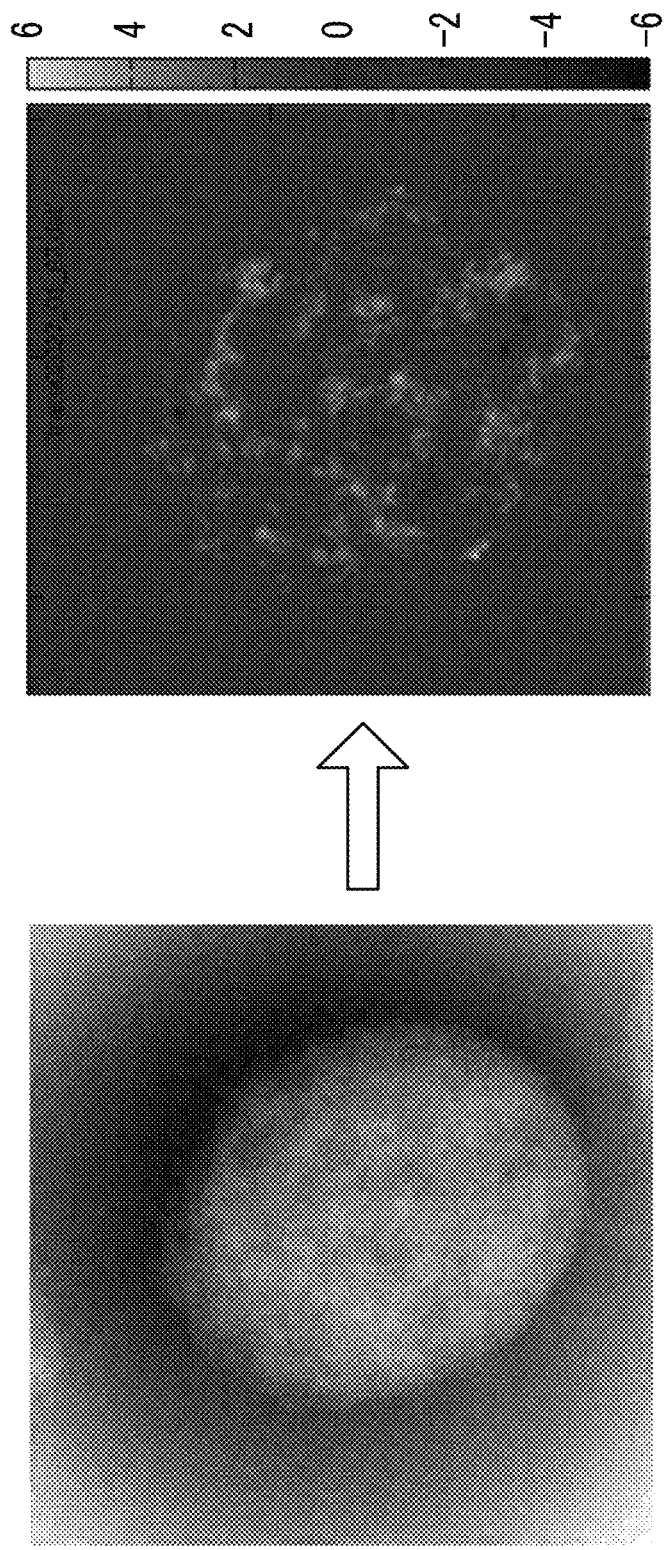
FIG. 16 shows an example of an image (right diagram) obtained by extracting a randomness of a phase difference amount (phase variation) from a phase difference image of a sphere.

For example, the index value indicating the randomness of the array of the phase difference amounts in a plurality of pixels constituting the phase difference image of the sphere may be derived on the basis of a shape component removal image obtained by performing process of removing a component depending on a shape of the sphere from the phase difference image of the sphere. Here, the component depending on the shape of the sphere is a curved surface which constitutes a basic shape of a sphere surface in the phase difference image of the sphere, and is gentle with respect to a pixel size, and a curved surface component which is derived as a result to approximation by a polynomial curved surface such as a quadratic function and a cubic function. By removing this component from the phase difference image of the sphere, the shape component removal image in which only randomness (phase variation)

of the phase difference amount in the phase difference image of the sphere is extracted can be obtained. FIG. 16 is a diagram showing an example of the shape component removal image (right in FIG. 16) from which the randomness (the phase variation) of the phase difference amount is extracted by performing process of removing the component depending on the shape of the sphere from the phase difference image (left in FIG. 16) of the sphere.

For example, the autocorrelation function derived for the shape component removal image (right in FIG. 16) can be used as the index value indicating the randomness of the array of the phase difference amounts in a plurality of pixels constituting the phase difference image of the sphere. That is, the autocorrelation function can quantify the randomness (phase variation) of the phase difference amount in the phase difference image of the sphere. Accordingly, it is possible to estimate the undifferentiated rate and survival rate of the cells for the sphere or the lot to be determined including the sphere on the basis of the autocorrelation function derived for the shape component removal image (right in FIG. 16). Further, by comparing the autocorrelation function obtained as described above with, for example, a reference sample in which the survival rate and undifferentiated rate of cells are known, it is possible to perform, for example, the quality determination for the sphere or the lot to be determined including the sphere.

In addition, the two-dimensional power spectrum derived for the shape component removal image (right in FIG. 16) can be used as the index value indicating the randomness of the array of the phase difference amounts in a plurality of pixels constituting the phase difference image of the sphere. A two-dimensional power spectrum P in a two-dimensional Fourier transform spectrum Φ (kx, ky) of the phase difference image Φ (x, y) is represented by the following Equation (5). Here, kx and ky are spatial frequencies.

$$P=|\Phi(kx,ky)|^2 \quad (5)$$

Figure 17:
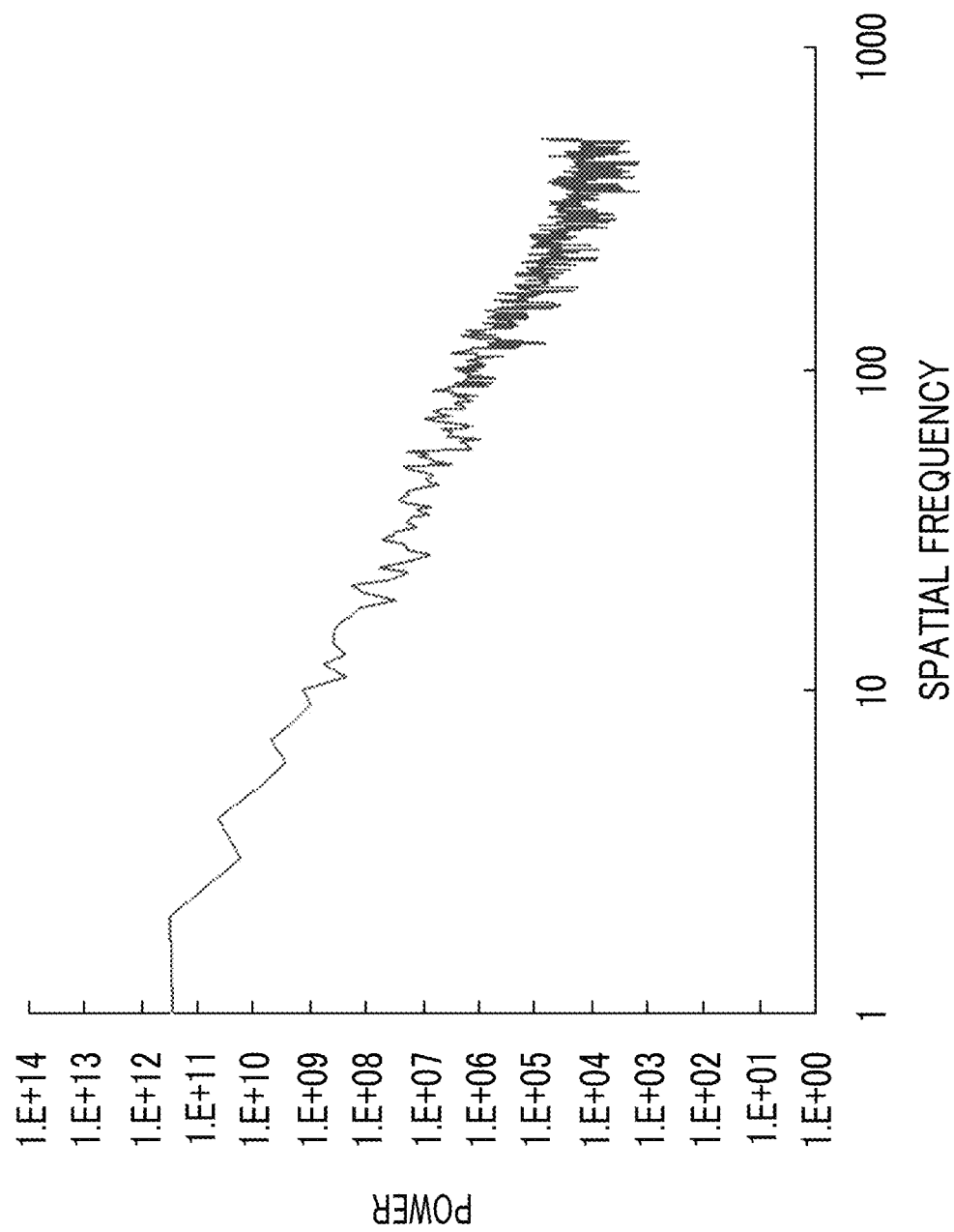
FIG. 17 is a diagram showing a two-dimensional power spectrum derived for an image that has been subjected to a process of removing a component depending on a shape of a sphere from a phase difference image of the sphere.

FIG. 17 is a diagram showing a two-dimensional power spectrum (set as ky=0) derived for the shape component removal image (right in FIG. 16). For example, the randomness (phase variation) of the phase difference amount in the phase difference image of the sphere can be quantified by a slope of the power spectrum exemplified in FIG. 17 and the function fitting. Accordingly, it is possible to estimate the undifferentiated rate and survival rate of the cells for the sphere or the lot to be determined including the sphere on the basis of the quantified values. Further, by comparing the two-dimensional power spectrum obtained as described above with, for example, a reference sample in which the survival rate and undifferentiated rate of cells are known, it is possible to perform, for example, the quality determination for the sphere or the lot to be determined including the sphere. It should be noted that in the example shown in FIG. 17, ky=0 is set, but $R=(kx^2+ky^2)^{1/2}$ may be set, and the power spectrum as shown in FIG. 17 may be used for R. In addition, from the Wiener-Khinchine theorem, the same can be applied to the autocorrelation function which is the inverse Fourier transform of the power spectrum.

EXPLANATION OF REFERENCES

1: imaging system
10: hologram optical system
11: laser light source
12: beam splitter
13: collimating lens
14: sample
15: objective lens
17: imaging lens
18: beam splitter
19: CMOS camera
20: optical fiber
21: collimating lens
34: dichroic mirror
500: computer
502: main memory
503: auxiliary storage device
504: communication interface
505: display unit
506: autofocus program
507: bus
$I_P$: phase difference image
θ: phase difference amount
$θ_B$: phase of background
$θ_S$: phase of region where sphere exist
$θ_k$: phase difference amount per 1 pixel
k: pixel
w: half-width of curve
λ: average phase fluctuation

What is claimed is:

1. A determination method comprising:
generating a phase difference image of an aggregate of a plurality of cells from a hologram obtained by imaging the aggregate;
deriving a first index value that indicates a randomness of an array of a phase difference amount in a plurality of pixels constituting the phase difference image; and
determining a state of the cells constituting the aggregate on the basis of the first index value,
wherein in a case where a minimum value of a phase difference amount in a predetermined range in a plurality of pixels constituting the phase difference image is denoted by $\Phi_0$ and a maximum value thereof is denoted by $\Phi_N$, a peripheral length of an equiphase line in a random phase Φ in the predetermined range is denoted by L (Φ), and an area of a region surrounded by an equiphase line having the peripheral length L (Φ) is denoted by A (Φ), an average phase fluctuation λ defined by the following Equation (I) is used as the first index value $$\lambda = \frac{1}{\Phi_N - \Phi_0} \int_{\Phi_0}^{\Phi_N} \frac{L(\Phi)^2}{4\pi A(\Phi)} d\Phi. \quad (I)$$

2. The determination method according to claim 1, wherein
the first index value is determined according to a degree of deviation from a circle of a shape of a region surrounded by an equiphase line connecting pixels of the same phase difference amount in the phase difference image.

3. The determination method according to claim 1, further comprising:
deriving the first index value on the basis of a shape component removal image that has been subjected to a process of removing a component depending on a shape of the aggregate from the phase difference image.

4. The determination method according to claim 1, further comprising:
performing a determination related to a survival rate of the cells constituting the aggregate on the basis of the first index value.

5. The determination method according to claim 2, further comprising:
performing a determination related to a survival rate of the cells constituting the aggregate on the basis of the first index value.

6. The determination method according to claim 3, further comprising:
performing a determination related to a survival rate of the cells constituting the aggregate on the basis of the first index value.

7. The determination method according to claim 1, further comprising:
performing a determination related to an undifferentiated rate of stem cells constituting the aggregate on the basis of the first index value, the stem cells being the cells constituting the aggregate.

8. The determination method according to claim 2, further comprising:
performing a determination related to an undifferentiated rate of stem cells constituting the aggregate on the basis of the first index value, the stem cells being the cells constituting the aggregate.

9. The determination method according to claim 3, further comprising:
performing a determination related to an undifferentiated rate of stem cells constituting the aggregate on the basis of the first index value, the stem cells being the cells constituting the aggregate.

10. The determination method according to claim 4, further comprising:
performing a determination related to an undifferentiated rate of stem cells constituting the aggregate on the basis of the first index value, the stem cells being the cells constituting the aggregate.

11. The determination method according to claim 5, further comprising:
performing a determination related to an undifferentiated rate of stem cells constituting the aggregate on the basis of the first index value, the stem cells being the cells constituting the aggregate.

12. The determination method according to claim 6, further comprising:
performing a determination related to an undifferentiated rate of stem cells constituting the aggregate on the basis of the first index value, the stem cells being the cells constituting the aggregate.

13. The determination method according to claim 1, further comprising:
deriving a second index value that indicates a correlation between the first index value and a particle diameter of the aggregate for a plurality of the aggregates included in a lot to be determined; and
performing a determination for the lot to be determined on the basis of the second index value.

14. The determination method according to claim 2, further comprising:
deriving a second index value that indicates a correlation between the first index value and a particle diameter of the aggregate for a plurality of the aggregates included in a lot to be determined; and
performing a determination for the lot to be determined on the basis of the second index value.

15. The determination method according to claim 3, further comprising:
deriving a second index value that indicates a correlation between the first index value and a particle diameter of the aggregate for a plurality of the aggregates included in a lot to be determined; and
performing a determination for the lot to be determined on the basis of the second index value.

16. The determination method according to claim 4, further comprising:
deriving a second index value that indicates a correlation between the first index value and a particle diameter of the aggregate for a plurality of the aggregates included in a lot to be determined; and
performing a determination for the lot to be determined on the basis of the second index value.

17. The determination method according to claim 5, further comprising:
deriving a second index value that indicates a correlation between the first index value and a particle diameter of the aggregate for a plurality of the aggregates included in a lot to be determined; and
performing a determination for the lot to be determined on the basis of the second index value.

18. The determination method according to claim 6, further comprising:
deriving a second index value that indicates a correlation between the first index value and a particle diameter of the aggregate for a plurality of the aggregates included in a lot to be determined; and
performing a determination for the lot to be determined on the basis of the second index value.

19. The determination method according to claim 13, further comprising:
performing a determination related to a survival rate of the cells included in the lot to be determined on the basis of the second index value.

20. The determination method according to claim 13, further comprising:
performing a determination related to an undifferentiated rate of stem cells included in the lot to be determined on the basis of the second index value, the stem cells being the cells constituting the aggregate.

* * * * *